United States Patent [19]

Borovian

[11] Patent Number: 4,607,036

[45] Date of Patent: Aug. 19, 1986

[54] PRESERVATIVE COMPOSITIONS EMPLOYING ANTI-MICROBIAL MORPHOLINE DERIVATIVES

[75] Inventor: Gayle E. Borovian, Dover, N.J.

[73] Assignee: Lever Brothers Company, New York, N.Y.

[21] Appl. No.: 768,938

[22] Filed: Aug. 26, 1985

Related U.S. Application Data

[63] Continuation of Ser. No. 561,845, Dec. 15, 1983, abandoned.

[51] Int. Cl.$^4$ ............................................. A01N 43/40
[52] U.S. Cl. ............................................. 514/277
[58] Field of Search ........................................ 514/227

[56] References Cited

U.S. PATENT DOCUMENTS

| | | | |
|---|---|---|---|
| 3,054,748 | 9/1962 | Hodge | 424/248.4 |
| 3,054,749 | 9/1962 | Bennett et al. | 424/248.4 |
| 3,192,163 | 6/1965 | Hodge | 424/248.4 |
| 3,647,703 | 3/1972 | Shema et al. | 424/248.4 |
| 3,759,828 | 9/1973 | Harrison | 252/33.4 |
| 3,860,516 | 1/1975 | Shema et al. | 424/347 |
| 3,862,034 | 1/1975 | Shema et al. | 424/347 |
| 3,881,008 | 4/1975 | Shema et al. | 424/329 |
| 3,897,554 | 7/1975 | Shema et al. | 424/304 |
| 3,917,834 | 11/1975 | Shema et al. | 424/337 |
| 3,929,563 | 12/1975 | Shema et al. | 424/270 |
| 4,101,433 | 7/1978 | Purcell et al. | 514/227 |
| 4,140,855 | 2/1979 | Shelton | 544/162 |

OTHER PUBLICATIONS

"Develop. Ind. Microbiol.", 1967, 9, pp. 448–476, by M. R. Rogers and A. M. Kaplan.
Bioban P-1487, Label.

*Primary Examiner*—Allen J. Robinson
*Attorney, Agent, or Firm*—Milton L. Honig; James J. Farrell

[57] ABSTRACT

A preservative composition is provided comprising 4-(2-nitrobutyl)morpholine, 4,4'-(2-ethyl-2-nitrotrimethylene)dimorpholine or mixtures thereof in an aqueous medium wherein the pH is less than 6.0. The perservative system is used in household or personal product composition containing a cleaning or conditioning amount of a surfactant.

8 Claims, No Drawings

PRESERVATIVE COMPOSITIONS EMPLOYING ANTI-MICROBIAL MORPHOLINE DERIVATIVES

This is a continuation, of Ser. No. 561,845, filed Dec. 15, 1983, now abandoned.

BACKGROUND OF THE INVENTION

1. Field of the Invention

This invention relates to a preservative system, household and personal product compositions containing the preservative, and a method for inhibiting the growth of microorganisms.

2. The Prior Art

Many household and personal product formulations, including their raw material components, are susceptible to microbiological contamination. Such compositions include dishwashing detergents, laundry liquids, fabric softeners and liquid soaps among others. Preservatives are frequently added to these formulations to protect them against microbial spoilage. Contaminating microbes are, however, adaptable. Given time, they often become immune to the preservative. Therefore, there is a continuing need for new preservatives.

Foremost among the preservatives for household products has been formaldehyde. Treatment with this chemical is effective and economical. Unfortunately, there have been some studies implicating formaldehyde with mutagenicity. Prudence has dictated a search for alternatives. Glutaraldehyde can substitute as a preservative but it must be employed at reasonably high levels and is 20 times more expensive per pound. Kathon CG, a trademark of Rohm & Haas, representing a mixture of 4 chloro-2-methyl-4-isothiazolin-3-one and 2-methyl-4-isothiazolin-3-one is effective in extremely low amounts. Yet, it costs 10 times as much as glutaraldehyde. Consequently, it is not as cost effective as traditional formaldehyde. Economical alternatives are needed.

Mixtures of 4-(2-nitrobutyl)morpholine (I) and 4,4'-(2-ethyl-2-nitrotrimethylene)dimorpholine (II) have been known for their anti-microbial properties in metalworking fluids and cooling waters for pulp and paper mills. Commercial literature prescribing the method of use for these mixtures recommends pH be controlled above 6.0. While the morpholine/dimorpholine mixtures have many desirable properties, they also suffer from several disadvantages. To obtain good anti-microbial activity, fairly high concentrations must be present. Patents and commercial literature suggest concentrations from 500 to 3000 ppm or higher are necessary to be effective. Cost and water-solubility are further problems.

Combinations of I and II with other anti-microbials have been described which overcome the problem of high concentration. In U.S. Pat. No. 4,101,433, a 3.5:1 mixture of I/II combined with tris(hydroxymethyl)nitromethane was disclosed to be active at 500 to 1500 ppm total concentration. Shema et al in a series of patents report increasing the effectiveness of 4-(2-nitrobutyl)morpholine by combination with either 2,4,5-trichlorophenol, 3,4',5-tribromosalicylanide, 2,2-dibromo-3-nitrilopropionamide, N-alkyl-dimethyl-benzyl ammonium chloride, a 2-methyl-4-isothiazolin-3-one calcium chloride mixture or hexachloro dimethyl sulfone; see U.S. Pat. Nos. 3,860,516, 3,862,034, 3,897,554, 3,881,008, 3,929,563 and 3,917,834, respectively. All these patents recognize the need to improve the efficacy of the generally desirable I and/or II compositions.

Accordingly, it is an object of this invention to provide an improved preservative containing I, II or mixtures thereof that is an effective anti-microbial agent at low concentrations.

Another object of this invention is to provide household and personal cleaning or conditioning compositions containing the preservative.

A further object of this invention is to provide a more efficient method for inhibiting the growth of microorganisms.

SUMMARY OF THE INVENTION

A preservative composition and method is provided comprising:
(i) 4-(2-nitrobutyl)morpholine, 4,4'-(2-ethyl-2-nitrotrimethylene)dimorpholine or mixtures thereof in an amount effective to kill or substantially inhibit the growth of microorganisms; and
(ii) water;
the composition characterized by a pH of less than 6.0.

Household or personal product compositions are also provided comprising:
(i) a surfactant in an amount effective to clean or condition a substrate;
(ii) 4-(2-nitrobutyl)morpholine, 4,4'-(2-ethyl-2-nitrotrimethylene)dimorpholine or mixtures thereof in an amount effective to kill or substantially inhibit the growth of microorganisms; and
(iii) water;
the composition characterized by a pH of less than 6.0.

DETAILED DESCRIPTION OF THE INVENTION

Mixtures of I and II are sold commercially for incorporation into metalworking fluids to prevent microbial attack. The compositions are also recommended for hydrocarbon fuel preservation and as slimicides in recirculating industrial water systems. The mixture is commercially available as Bioban ® P-1487 from the Angus Chemical Company, Northbrook, Ill. The ratio of I to II in the mixture is 7:2. Hereinafter this mixture will be referred to as P-1487. The Bioban ® P-1487 label recommends dosages ranging from 500 ppm to 3000 ppm. P-1487 is said to be stable where pH is maintained above 6.

In view of the quoted properties of P-1487, it was surprising to find this mixture stable at pH below 6, preferably below 5.6, and in essentially non-hydrocarbon bearing household and personal product compositions. Moreover, it was even more surprising to observe that the effectiveness of these compounds increased at low pH. Consequently, only very low concentrations of P-1487 were necessary to adequately preserve water-based formulations.

Both compounds I and II apear to be equally effective as anti-microbial agents. They may be used separately or in combination at any ratio of concentrations.

To be effective, I and II and mixtures thereof such as P-1487 are active in killing or substantially inhibiting microorganisms at a use level of from about 0.1 ppm to about 120 ppm. Preferably, the level of preservative should range from 10 to 90 ppm.

Among the household and personal products that were found suitably preserved with I, II and P-1487 were dishwashing detergents, fabric softeners, liquid soaps, laundry detergents, shampoos, hair conditioners and cosmetics. Besides the preservative, these formulations all have one element in common. They all contain a surface active compound in a quantity sufficient to effect cleaning or conditioning of a substrate. Surfactants are here not merely present as emulsifiers.

The invention contemplates household and personal products having anionic, nonionic, cationic, amphoteric, zwitterionic or mixtures of these type surfactants.

Anionic surfactants can be broadly described as surface active chemicals with a negatively charged functional group(s). An important class within this category are the water-soluble salts, particularly the alkali metal salts, of organic sulfur reaction products having in their molecular structure an alkyl radical containing from about 8 to about 22 carbon atoms and a radical selected from the group consisting of sulfonic acid and sulfuric acid ester radicals. Such surfactants are well known in the detergent art; they are described at length in "Surface Active Agents and Detergents", Vol. II, by Schwartz, Perry and Berch, Interscience Publishers, Inc., 1958, incorporated by reference.

Among the useful anionic surfactants are the alkyl sulfates, alkyl ether sulfates, higher alkylbenzene sulfonates, higher linear olefin sulfonates, dialkyl sulfosuccinates and acyl esters of isethionates.

Nonionic surfactants can be broadly defined as surface active chemicals which do not contain ionic functional groups. An important group within the class are those produced by the condensation of alkylene oxide with aliphatic or alkyl aromatic alcohols or acids. Illustrative are the polyoxyethylene or polyoxypropylene condensates of $C_8$-$C_{18}$ aliphatic carboxylic acids, alcohols or alkyl phenols. Block or random copolymers of polyoxyethylene and polyoxypropylene are further suitable examples.

Many cationic surfactants are known in the art, and almost any cationic surfactant having at least one long chain alkyl group of about 10 to 24 carbon atoms in the molecule is suitable. Such compounds are described in "Cationic Surfactants", Jungermann, 1970, incorporated by reference. Illustrative of this class are noncyclic quaternary ammonium salts having at least one $C_{12-30}$ alkyl chain, substituted polyamine salts, $C_{8-25}$ alkyl imidazolinium salts and $C_{12-20}$ alkyl pyridinium salts.

Ampholytic and zwitterionic surfactants are also within the purview of this invention. Examples of ampholytic surfactants include derivatives of aliphatic secondary and tertiary amines having a $C_{8-18}$ aliphatic radical and containing an anionic water-solubilizing group, i.e., carboxy, sulpho, sulphato, phosphato or phosphono. Examples of compounds falling within this definition are sodium 3-dodecylamino proprionate and sodium 2-dodecylamino propane sulfonate.

Zwitterionic surfactants can be broadly described as derivatives of aliphatic quaternary ammonium, phosphonium and sulphonium salts in which there is a $C_{8-18}$ aliphatic radical containing an anionic water-solubilizing group, e.g., carboxy, sulpho, sulphato, phosphato or phosphono. Examples of compounds falling within this definition are 3-(N,N-dimethyl-N-hexadecylammonio)-propane-1-sulfonate and 3-(N,N-dimethyl-N-hexadecylammonio)-2-hydroxypropane-1-sulfonate.

Normally, the percentage of surfactant can range from about 1% to about 50% by weight of the household or personal product. Where the product has a cationic surfactant such as in a fabric softening formulation, the preferable concentration range of cationic surfactant is from about 3% to about 15%. Where anionic and nonionic surfactants are employed in dishwashing or laundry detergent formulations, for instance, the preferable ranges are from about 10% to 30% of anionic and from about 3% to 15% of nonionic surfactant per weight of the detergent product. Where anionic surfactants are used in shampoo formulations or hair conditioners, the anionic surfactant concentration level preferably ranges from about 10 to 30%.

Water is another essential component of the household or personal products of this invention. It can range in an amount from about 20% to 97%, depending upon the particular type of formulation. Typically, fabric softening compositions have water present in an amount over 90%. These compositions will also have a pH of around 3.5. Dishwashing formulations generally require an amount of water ranging from about 50 to 70%. Liquid laundry detergents will usually contain from about 40 to 80% water. Shampoos include water to the extent of from about 20 to 70%.

Hydrocarbons, except for possibly very minor amounts of highly volatile propellant hydrocarbon for spray application, are essentially absent from these preservative systems and formulations. Consequently, the preservative system and formulation will contain less than 1% of hydrocarbon oils.

The following examples will more fully illustrate the embodiments of this invention. All parts, percentages and proportions referred to herein and in the appended claims are by weight unless otherwise illustrated.

EXAMPLE 1

Three household product formulations were prepared to evaluate the preservative systems of this invention. The composition of a fabric conditioning formulation A and two dishwashing formulations B and C are illustrated below.

| FABRIC SOFTENING FORMULATION A | |
|---|---|
| Components | % Active |
| Di(hydrogenated tallow) dimethyl ammonium Chloride | 2.91 |
| Dicoco dimethylammonium Chloride | 0.59 |
| Ceranine HC* | 2.53 |
| Neodol 25-9** | 0.25 |
| Citric acid | 0.243 |
| Sodium citrate | 0.012 |
| Colorant | 0.0033 |
| Fabric brightening agent | 0.144 |
| Perfume | 0.150 |
| Water | to 100% |
| Final pH | 3.4 ± 0.3 |

*Complex reaction product of 2 moles of an acid having the formula $R_1COOH$ wherein $R_1$ is an aliphatic hydrocarbon group containing from 15 to 19 carbon atoms and an alkaline diamine of the formula $H_2N-R_2-NR_3H$ wherein $R_2$ is an alkaline group containing from 1 to 2 carbon atoms and $R_3$ is a hydroxy alkyl group containing from 1 to 3 carbon atoms.
**A $C_{12}$-$C_{15}$ fatty alcohol ethoxylated with 9 moles of ethylene oxide.

| DISHWASHING DETERGENT FORMULATIONS B AND C | | |
|---|---|---|
| | % Active | |
| Components | B | C |
| Ammonium linear alkylbenzene sulfonate | 22.20 | 22.20 |
| Ammonium fatty alcohol ethoxysulfate | 3.40 | 4.40 |
| Lauric/myristic diethanolamide | 1.40 | 0.90 |
| Ammonium xylene sulfonate | 5.00 | 5.00 |
| Lytron Opacifier* | 0.40 | 1.00 |

-continued

DISHWASHING DETERGENT FORMULATIONS B AND C

| Components | % Active B | C |
|---|---|---|
| Water and miscellaneous | to 100% | to 100% |

*Modified polystyrene (solids 39–41%)

EXAMPLE 2

Contaminated Product Treatment (CPT) studies were conducted in which 75 gram samples of microorganism bearing Example 1 formulations were treated with an over-the-side addition of various preservative levels of P-1487. Preservative activity was evaluated microbiologically on treated and control samples. Activity was recorded initially and after appropriate storage periods. Samples were evaluated daily for the first three days. Thereafter, evaluations were done weekly. The level of preservative considered to be effective in commercial products provides 10 gram sterility within a three day period.

TABLE 1
BIOBAN ® P-1487:
CONTAMINATED PRODUCT TREATMENT

| | | Log Count/10 g | | | |
|---|---|---|---|---|---|
| | Initial | One Day | Two Days | Three Days | 1 to 2 Weeks |
| Formulation A | | | | | |
| Preservative Level (ppm active) | | | | | |
| 18 ppm | 6 | 5 | 3 | 0 | 0 |
| 46 | 6 | 5 | 0 | 0 | 0 |
| 90 | 6 | 4 | 0 | 0 | 0 |
| 120 | 6 | 0 | 0 | 0 | 0 |
| 180 | 6 | 0 | 0 | 0 | 0 |
| 240 | 6 | 0 | 0 | 0 | 0 |
| Control | 6 | 5 | 6 | 7 | 8 |
| Product Contaminants | Gram-negative bacteria (*Pseudomonas cepacia*) | | | | |
| Formulation B | | | | | |
| Preservative Level (ppm active) | | | | | |
| 18 ppm | 5 | 1 | 0 | 0 | 0 |
| 46 | 5 | 0 | 0 | 0 | 0 |
| 90 | 5 | 0 | 0 | 0 | 0 |
| 120 | 5 | 0 | 0 | 0 | 0 |
| 180 | 5 | 0 | 0 | 0 | 0 |
| 240 | 6 | 0 | 0 | 0 | 0 |
| Control | 6 | 6 | 5 | 5 | 5 |
| Product Contaminants | Yeasts | | | | |
| Formulation C | | | | | |
| Preservative Level (ppm active) | | | | | |
| 18 ppm | 5 | 1 | 0 | 0 | 0 |
| 46 | 5 | 1 | 0 | 0 | 0 |
| 90 | 5 | 0 | 0 | 0 | 0 |
| 120 | 5 | 0 | 0 | 0 | 0 |
| 180 | 5 | 0 | 0 | 0 | 0 |
| 240 | 6 | 0 | 0 | 0 | 0 |
| Control | 6 | 5 | 5 | 5 | 5 |
| Product Contaminants | Yeasts | | | | |

As shown on Table 1, 18 ppm of P-1487 exhibited antimicrobial activity in Formulations A, B and C. This level of active appears to be ideal for Formulation A, i.e., elimination of contaminants within three days. However, a level lower than 18 ppm of active would be effective in Formulations B and C as counts were drastically reduced in these samples within one day.

EXAMPLE 3

Bioban ® P-1487, applied at pH 5.5, is not only successful as an anti-microbial for finished formulations, but can be used to preserve individual raw material components. For example, a yeast and bacteria contaminated opacifier called Lytron was successfully purged of microbiological contaminants. Lytron is a modified polystyrene latex containing 39–41% solids manufactured by the Monsanto Company. The results of CPT studies are listed in Table 2. P-1487 at a level of 18 ppm is sufficient to eliminate yeast and bacterial infestation. Preservative concentrations significantly below 18 ppm would also be expected to be effective.

TABLE 2
BIOBAN ® P-1487:
CONTAMINATED PRODUCT TREATMENT
LYTRON OPACIFIER - pH 5.5

| | | Log Count/10 g | | | |
|---|---|---|---|---|---|
| | Initial | One Day | Two Days | Three Days | 1 to 2 Weeks |
| Preservative Level (ppm active) | | | | | |
| 18 ppm | 5 | 0 | 0 | 0 | 0 |
| 46 | 5 | 0 | 0 | 0 | 0 |
| 90 | 5 | 0 | 0 | 0 | 0 |
| 120 | 5 | 0 | 0 | 0 | 0 |
| 180 | 5 | 0 | 0 | 0 | 0 |
| 240 | 6 | 0 | 0 | 0 | 0 |
| Control | 5 | 5 | 8 | 8 | 7 |
| Product Contaminants | Yeast, Gram-negative bacteria and Gram-variable Actinomyces-like bacteria | | | | |

EXAMPLE 4

Gradient Plate evaluations were performed on the P-1487 mixture and pure compound I. An objective of these experiments was to determine the relative activity of compound I and II. Synthesis of 2-nitrobutyl morpholine (I) was accomplished starting with 1-nitropropane, morpholine and formaldehyde. The procedure was that described by Shelton in U.S. Pat. No. 4,140,855, herein incorporated by reference.

GRADIENT PLATE PROCEDURE

The Gradient Plate procedure is a method for determining preservative activity as measured in "Minimum Inhibitory Concentration" (MIC) values. The method was described by Janet C. Curry in the 1965 CSMA proceedings, 52nd Annual Meeting. In accordance with this method, a square phage-type petrie dish was prepared containing a base layer of Tryptic Soy Agar (supplied by Difco) hardened into the form of a wedge. Agar pH levels were controlled by inclusion of citric acid. A second layer of agar was applied containing specific levels of preservative. This top layer was hardened holding the plate level. Test agent from the top layer diffuses into the base layer causing a concentration gradient on the surface. Preservatives were prepared having gradient plate dilutions ranging from 1 to 500 ppm active material.

Eleven product/raw material isolates (contaminants) were carried on agar slants (slant washings provided $10^5$ to $10^8$ cells/ml). Organisms were then streaked across the surface of the agar.

A streaking apparatus was employed which provided simultaneous and multiple innoculation. Plates were incubated at 32° C. for 3 days. Resultant streaks were measured in millimeters to the point of inhibition. MIC values for P-1487 or compound I were determined by direct proportion of the gradient plate concentration of preservative to the growth front measurement.

MIC values represent the lowest level of active which inhibits organism growth. A broad spectrum of organisms were evaluated. They consisted of a variety of product isolates and American Type Culture Collection (ATCC) organisms generally used for comparison in gradient plate tests.

yeasts, molds and gram positive and gram negative bacteria. They function as preservatives in a wide range of household and personal product formulations and raw material components. Generally, they are effective at concentrations starting at less than 20 ppm.

EXAMPLE 5

The following shampoo and hair conditioner formulations illustrate another application for the preservative system of this invention.

TABLE 3

| | | GRADIENT PLATE RESULTS | | | |
|---|---|---|---|---|---|
| | | MEDIA pH 4.5 MIC Values in ppm | | MEDIA pH 7.2 MIC Values in ppm | |
| SOURCE | ISOLATE | Bioban P-1487 | 4-2(2-nitrobutyl) morpholine | Bioban P-1487 | 4-(2-nitrobutyl) morpholine |
| Fabric Softeners | | | | | |
| STA PUF* (pH 2.5) | yeast | 10 | 10 | 33 | 33 |
| Formulation A | Pseudomonas cepacia (Gram negative rod) | 25 | 25 | 89 | 93 |
| | Aspergillus (mold) | 22 | 16 | 250 | 200 |
| Dishwashing Detergents | | | | | |
| Formulation B | actinomyces-type** | 10 | 10 | 220 | 170 |
| | yeast | 5.0 | 10 | 19 | 25 |
| Formulation C | actinomyces-type | 10 | 10 | 360 | 330 |
| | actinomyces-type | 10 | 10 | 36 | 67 |
| | yeast | 10 | 10 | 72 | 67 |
| Formulation D | yeast | 2.5 | 2.5 | 8.5 | 8.3 |
| Raw Material | | | | | |
| Lytron (pH 5.2) | actinomyces-type | 25 | 25 | 107 | 111 |
| | yeast | 8 | 8 | 38 | 38 |
| Std. G.P. Organisms (ATCC cultures) | | | | | |
| Staphylococcus aureus (#6538) (Gram positive cocci) | | 5 | 5 | 56 | 67 |
| Escherichea coli (#10530) (Gram negative rod) | | 10 | 10 | 73 | 84 |
| Candida albicans (#10231) (yeast) | | 25 | 25 | 120 | 110 |

NOTES:
1. *A. E. Staley Mfg. Co., Oak Brook, Illinois; contains quaternary ammonium surfactant.
2. **actinomyces-type of bacteria are environmentally found Gram variable-filamentous rods.
3. Samples were corrected to 100% active for GP testing and dilutions ranging from 500 to 1 ppm active were prepared.

| DISHWASHING FORMULATION D | |
|---|---|
| Components | % Active |
| Ammonium linear alkylbenzene sulfonate | 17.5 |
| Ammonium fatty alcohol ethoxy sulfate | 12.0 |
| Sodium xylene sulfonate | 6.0 |
| Lauric/myristic monoethanolamide | 4.0 |
| Citric Acid | 0.34 |
| Perfume | 0.25 |
| Colorant and miscellaneous additives | 5.14 |
| Water | to 100% |

Both Bioban® P-1487 and compound I exhibited similar activity in all formulations at both pH levels as seen from Table 3. Consequently, compounds I and II and mixtures are about equally effective in controlling microorganism growth. Preservative activity was found for fabric softener compositions, dishwashing detergents and raw material components such as Lytron opacifier.

The preservatives were evaluated at pH 4.5 and 7.3 to determine pH effect. MIC values obtained against the organisms in the low pH environment were considerably better (lower) than those obtained in the higher pH media. MIC values for P-1487 and I ranged from 5 to 25 ppm at pH 4.5. In contrast, MIC values ranged from 8.3 to 360 ppm at pH 7.3.

Compounds I and II, as shown by the data in Table 3, provide excellent broad spectrum anti-microbial activity under low pH conditions. They are effective against

| HAIR SHAMPOO | |
|---|---|
| Component | Weight % |
| Triethanolamine lauryl sulfate | 17.0 |
| Cocomonoethanolamide | 3.0 |
| Corn Syrup, 42 dextrose equiv. (80%) | 20.5 |
| Dimethyl Polysiloxane | 1.0 |
| Alcohol, SDA 40 | 9.0 |
| Cationic cellulose (Polymer JR, Union Carbide) | 0.5 |
| Vinyl carboxy polymer (Carbopol 941, B. F. Goodrich) | 0.75 |
| Hydroxypropyl methyl cellulose | 0.25 |
| Preservative II | 20 ppm |
| Water | to 100 |

| HAIR CONDITIONER | |
|---|---|
| Component | Weight % |
| Stearyl trimethyl ammonium chloride (25% active) | 5.0 |
| Stearyl alcohol | 4.0 |
| Propylene glycol | 2.0 |
| Methyl glucose ether/20 moles propylene oxide | 1.5 |
| Lanolin ether/20 moles propylene oxide | 1.5 |
| Polymer JR | 0.75 |
| Perfume | 0.20 |
| Emulsifier | 0.10 |
| Preservative I | 20 ppm |

-continued

HAIR CONDITIONER

| Component | Weight % |
|---|---|
| Water | to 100 |

EXAMPLE 6

The following illustrates a liquid laundry detergent formulation containing the preservative system of this invention.

| Component | Weight % |
|---|---|
| Sodium linear alkylbenzene sulfonate | 17.0 |
| Neodol 23–6.5 ($C_{12-13}$ fatty alcohol ethoxylated with 6.5 moles ethylene oxide) | 10.0 |
| Sodium xylene sulfonate | 5.0 |
| Sodium citrate | 5.0 |
| Monoethanolamide | 2.0 |
| Methocel A-100 (methylcellulose) | 0.5 |
| Perfume | 0.15 |
| Opacifier | 0.05 |
| Preservative | |
| Compound I | 10 ppm |
| Compound II | 10 ppm |
| Water | to 100 |

The foregoing description and examples illustrate selected embodiments of the present invention. In light thereof, various modifications will be suggested to one skilled in the art, all of which are within the spirit and purview of this invention.

What is claimed is:

1. A household or personal product composition comprising:
   (i) from about 1 to 50% of surfactant to clean or condition a substrate;
   (ii) from about 0.1 to about 120 ppm of an antimicrobial agent effective against yeasts, molds or bacteria, selected from the group consisting of 4-(2-nitrobutyl)morpholine, 4,4'-(2-ethyl-2-nitrotrimethylene)dimorpholine and mixtures thereof, wherein said mixtures are in a ratio of 1:20 to 20:1; and
   (iii) from about 20 to 97% water;

the composition characterized by a pH ranging from 5.6 to 3.5 and containing less than 1% of hydrocarbon oils.

2. A composition according to claim 1 wherein the pH is less than 5.6.

3. A composition according to claim 1 wherein there is present a mixture of 4-(2-nitrobutyl)morpholine and 4,4'-(2-ethyl-2-nitrotrimethylene)dimorpholine in a ratio from about 1:20 to about 20:1.

4. A composition according to claim 1 wherein the surfactant is selected from anionic, nonionic, cationic, amphoteric, zwitterionic surfactants or mixtures thereof.

5. A method for preserving an aqueous household or personal product containing less than 1% of a hydrocarbon oil, the method comprising incorporating into the product a composition comprising from about 0.1 to about 120 ppm of an antimicrobial agent effective against yeasts, molds or bacteria, selected from the group consisting of 4-(2-nitrobutyl)morpholine, 4-4'-(2-ethyl-2-nitrotrimethylene)dimorpholine and mixtures thereof, wherein said mixtures are in a ratio of 1:20 to 20:1 and water, the composition characterized by a pH ranging from 5.6 to 3.5.

6. A method according to claim 5 wherein the water is present in an amount from about 20 to 97%.

7. A method according to claim 5 wherein the pH is less than 5.6.

8. A method according to claim 5 wherein there is present a mixture of 4-(2-nitrobutyl)morpholine and 4,4'-(2-ethyl-2-nitrotrimethylene)dimorpholine in a ratio from about 1:20 to about 20:1.

* * * * *